United States Patent [19]

Brizzolara

[11] Patent Number: 6,127,130
[45] Date of Patent: Oct. 3, 2000

[54] MULTIASSAY METHOD FOR DETERMINING THE CONCENTRATIONS OF ANTIGENS AND INTERFERANTS

[75] Inventor: Robert A. Brizzolara, Beltsville, Md.

[73] Assignee: The United States of America as represented by the Secretary of the Navy, Washington, D.C.

[21] Appl. No.: 09/042,046

[22] Filed: Mar. 13, 1998

[51] Int. Cl.[7] .................. G01N 33/577; G01N 33/53; G01N 33/537; G01N 33/543; C07K 16/44

[52] U.S. Cl. .............. 435/7.1; 435/7.5; 435/7.93; 435/7.9; 435/7.94; 435/7.92; 435/29; 435/174; 435/517; 435/805; 435/960; 435/961; 435/240.27; 435/970; 435/973; 435/975; 436/169; 436/170; 436/810; 436/528; 436/529; 436/530; 436/501; 436/518; 436/538; 436/542; 436/525; 436/533; 436/541; 436/164

[58] Field of Search ................ 435/7.1, 962, 7.5, 435/7.93, 29, 7.9, 7.94, 7.92, 970, 973, 975, 805, 174, 517, 960, 961, 240.27; 23/230 B; 436/525, 172, 169, 170, 810, 528–530, 501, 518, 538, 542, 533, 541, 164; 422/56–58, 61; 128/630, 653.1; 364/413.01, 413.02, 413.13; 395/21, 23, 24; 530/388.9, 389.8

[56] References Cited

U.S. PATENT DOCUMENTS 4,313,734  2/1982  Leuvering ...................... 23/230 B
5,158,869  10/1992  Pouletty et al. ................ 435/7.9
5,589,401  12/1996  Hansen et al. ................. 436/525
5,691,148  11/1997  Friedman et al. .............. 435/7.1
5,891,641  4/1999  Prusiner et al. ............... 435/7.1

OTHER PUBLICATIONS

Colin Tillyer, Clinical Chemistry 36(2), pp. 307–312, (1990). Calibration in Three Dimensions: Optimizing a two–Parameter Calibration Technique to Extend the Range of an Immunoturbidimetric Urinary Albumin Assay into Antigen Excess, Jan. 1990.

*Primary Examiner*—Christopher L. Chin
*Assistant Examiner*—Lisa V. Doniels-Cook
*Attorney, Agent, or Firm*—John Forrest; Roger D. Johnson

[57] ABSTRACT

A method of determining the concentration of a sample antigen in the presence of an interferant by (1) running two immunoassays on the sample: one assay where the interferant influences the binding of both the sample antigen and a labeled antigen and a second assay where the interferant influences the binding of the sample antigen but not the labeled antigen;

(2) obtaining a plot of the possible sample antigen concentrations versus the possible interferant concentrations corresponding to the readout for the sample for each of the two immunoassays; and (3) determining the sample antigen concentration and the interferant concentration which correspond to the point that appears in both the immunoassays plots.

7 Claims, 3 Drawing Sheets

MULTIASSAY METHOD FOR DETERMINING THE CONCENTRATIONS OF ANTIGENS AND INTERFERANTS

BACKGROUND

This invention relates to assays and more particularly to immunoassays for the detection of antigens.

Presently, immunoassays are capable of detecting only one antigen (if the antibody is cross-reactive, the assay might detect a set of chemically similar antigens). If there are chemical species present in the sample which affect the affinity of the antibody for its antigen (interferants), the results of the assay will change. If the sample is an unknown, there will be no way of realizing that the results of the assay have been compromised. For example, the commercially available immunoassays for petroleum in water use a single conventional test such as a competition immunoassay, to give the petroleum content of water for concentrations in the ppm (parts per million) range. The antibodies in these assays bind a specific constituent of the petroleum, usually BTEX (benzene, toluene, ethylbenzene, and xylene). However, petroleum contains other species (such as alkanes) that change the antibody affinity for the BTEX, and thus change the results of the assay. In the protocol recommended by the manufacturer of these kits, the calibration is performed against a specific petroleum product (i.e., gasoline, kerosene, home heating fuel, etc). This assumes that one knows before hand what type of petroleum product is in the sample. If not, the result of the assay is inaccurate. A modification of the technique to quantify the interferants would be extremely valuable in obtaining additional quantitative information from the assay.

SUMMARY

Accordingly, an object of this invention is to provide a method of accurately quantifying a known antigen and a known interferant in a sample containing a mixture of the antigen and interferant.

Another object of this invention is to provide a method of determining the concentration of a known antigen in the presence of an unknown interferant.

A further object of this invention is to provide a method of determining information about the binding activity of an unknown antigen and an unknown interferant in a sample containing a mixture of the antigen and the interferant.

These and other objects of this invention are achieved by providing
a method for determining the concentrations of a known antigen and a known interferant in a sample comprising:
  A. generating a 3-dimensional calibration curve for a competition immunoassay which shows the assay readout for points on a matrix of the antigen concentration versus the interferant concentration;
  B. generating a 3-dimensional calibration curve for a non-competition immunoassay selected from the group consisting of inhibition immunoassays and sandwich immunoassays which shows the assay readout for points on a matrix of the antigen concentration versus the interferant concentration;
  C. performing the competition immunoassay on the sample using the same conditions and parameters used in generating the 3-dimensional calibration curve in step A to obtain a competition immunoassay readout for the sample;
  D. finding the matrix points on the 3-dimensional calibration curve for the competition immunoassay (step A) which have the same readout as the sample (step C) and using the points to form a 2-dimensional curve of the antigen concentration versus the interferant concentration for the competition readout value for the sample;
  E. performing the non-competition immunoassay on the sample using the same conditions and parameters used in generating the 3-dimensional calibration curve in step B to obtain a non-competition immunoassay readout for the sample;
  F. finding the matrix points on the 3-dimensional calibration curve for the non-competition immunoassay (step B) which have the same readout as the sample (step E) and using the points to form a 2-dimensional curve of the antigen concentration versus the interferant concentration for the non-competition immunoassay readout value for the sample; and
  G. finding the point of intersection between the 2-dimensional competition immunoassay curve (step D) and the 2-dimensional non-competition immunoassay curve (step F) and reading the antigen concentration and the interferant concentration corresponding to this point.

If the antigen is known but the interferant is unknown, a substitute known interferant is used with the known antigen to generate the 3-dimensional calibration curves for the competition and the non-competition immunoassays. Otherwise, the method is performed as described above. The resulting matrix point in step G gives the concentration of the known antigen and the concentration of the substitute known interferant which produces the same influence or interference as the unknown concentration of the unknown interferant in the sample.

If the antigen is unknown and the interferant is known, a substitute known antigen is used with the known interferant to generate the 3-dimensional calibration curves for the competition and the non-competition immunoassays. Otherwise, the method is performed as described above. The resulting matrix point in step G gives the interferant concentration and concentration of the substitute known antigen which has the same immunoassay activity as the unknown concentration of the unknown antigen in the sample.

Even if both the antigen and the interferant are unknown, the above method can be adapted to provide some information. A substitute known antigen and a substitute known interferant are used to generate the 3-dimensional calibration curves for the competition and the non-competition immunoassays. Otherwise, the method is performed as described above. The resulting matrix point in step G gives the concentrations of the substitute known antigen and the substitute known interferant which give the equivalent results as the unknown concentrations of the unknown antigen and the unknown interferant in the sample.

BRIEF DESCRIPTION OF THE FIGURES

A more complete understanding of the invention and many of the attendant advantages thereto will be readily appreciated as the same becomes better understood by reference to the following description when considered in connection with the accompanying figures wherein:

FIGS. 1 through 3 are discussed in more detail in the specification and especially in the examples.

DESCRIPTION

Figure 1:
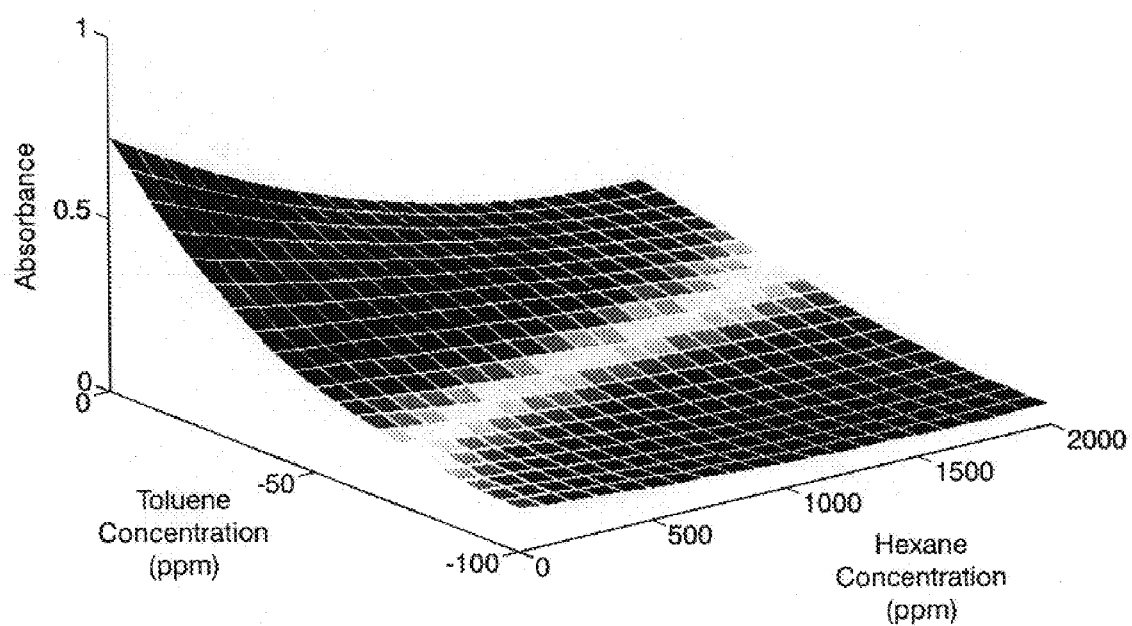
FIG. 1 is a 3-dimensional calibration curve for a competition immunoassay plotting optical absorbance of the assay solution versus toluene (antigen) concentration versus n-hexane (interferant) concentration.

The present invention provides a method for more accurately determining the concentration of an antigen in the presence of an interferant. The antigen is the target chemical species which is bound to the detecting antibody. The interferant is a chemical substance which does not bind with the antibody but which interferes with the ability of the antibody to bind with the target antigen. Because the interferant does not directly react with the antibody, a single conventional immunoassay will not be able to detect the presence of an interferant. In the present invention an multiassay protocol is used. A competition immunoassay and a non-competition (inhibition or sandwich) immunoassay arc run. If these assays give the same result, no interferant is present. If not, the different assay results are used to determine the antigen concentration and the interferant concentration.

The multiassay protocol of the present invention uses conventional immunoassays such as competition, inhibition (or blocking), and sandwich immunoassays in their usual way. In other words, no modification of the physical procedure is required. The normal incubation times and temperatures, substrates, antibodies, labels and methods of reading labels, etc. are used.

The multiassay protocol differs from conventional immunoassay procedures in two critical respects. First, the results of two different immunoassays are used to determine the antigen concentration. One of the immunoassays must be a competition immunoassay and the other must be a non-competition (i.e., inhibition or sandwich) immunoassay. In the competition immunoassay, the interferant interferes with the binding of the labeled antigen to the antibody; but in the non-competition immunoassays, it does not. Second, the standard or calibration curves for each of the immunoassays in the multiassay protocol are different from those used in conventional immunoassays. Conventional immunoassays use a 2-dimensional standard curve plotting a readout (e.g., optical absorbency) versus antigen concentration. For each of the immunoassays of the present multiassay protocol, a 3-dimensional standard or calibration curve plotting readout versus antigen concentration versus interferant concentration is required. In general, if X standard samples are needed to produce a 2-dimensional curve for a conventional immunoassay protocol, then $2X^2$ standard samples will be needed to produce the two 3-dimensional calibration curves need for the present multiassay protocol. The added time and expense of running the additional standard samples can be reduced by the use of multi-welled substrates to run parallel tests.

Again, one of the two immunoassays must be a competition immunoassay. In the competition immunoassay, the antibody is immobilized on the surface of a substrate. Then the sample and a labeled antigen are added simultaneously. The antigen in the sample and the labeled antigen compete for antibody binding sites on the substrate surface. After incubation, the surface is washed to remove the unbound antigens and the interferant, and then the labeled antigen on the substrate is read. The strength of the readout signal is inversely proportional to the original antigen concentration in the sample. Note that in the competition immunoassay, the interferant interferes with the binding of the labeled antigen as well as the sample antigen.

The other immunoassay must be a non-competition (inhibition or sandwich) immunoassay. In the inhibition immunoassay, the antibody is immobilized on the surface of a substrate. Then the sample is added and incubated. The unbound antigen and interferant of the sample are then washed away. A labeled antigen is then added and incubated. The unbound labeled antigen is then washed away and the labeled antigen bound to the antibody on the surface is read. The strength of the readout signal is inversely proportional to the original antigen concentration in the sample. In contrast to the competition immunoassay, the interferant in the inhibition immunoassay does not influence or interfere with the binding of the labeled antigen to the antibody. In the sandwich immunoassay, an antibody is immobilized on the surface of a substrate. Then the sample is added and incubated. The unbound antigen and interferant of the sample are then washed away. A labeled antibody specific to the antigen is then added and incubated. The unbound labeled antibody is then washed away and the bound labeled antibody is then read. The strength of the readout signal is directly proportional to the original antigen concentration of the sample. In the sandwich immunoassay, the interferant interferes with the binding of the antigen to the unlabeled antibody attached to the substrate, but the interferant is not present to interfere with the binding of the labeled antibody to the antigen.

Labels which may be used include fluorescent labels such as fluorescein isocyanate, radioisotopic labels such as $^{125}I$, colloidal gold particle labels, and enzymatic labels such as horseradish peroxidase, alkaline phosphatase, galactosidase, urease, and glucose oxidase. The enzymatic labels are preferred with ELISA (enzyme-linked immunosorbent assay) labels being more preferred. The fluorescent labels are read using fluorometry and the radioisotopic labels are read using a scintillation counter. Colloidal gold particles can be detected by their color, or using a scanning electron microscope. The enzymatic label produces a color change which can be detected by a spectrophotometer. Often a substrate is added which reacts with the enzymatic label to produce the color change. Readout is a generic term which refers to the output of any of these or similar devices which is quantitatively measuring the amount of label present in the sample being assayed.

Figure 2:
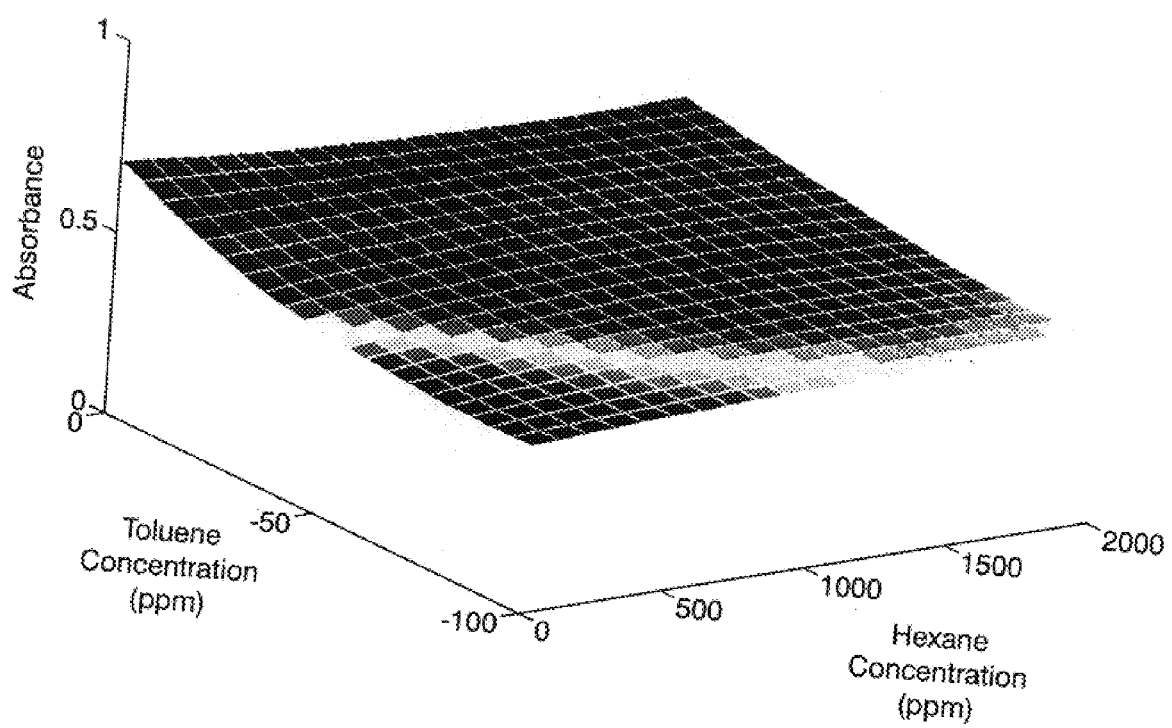
FIG. 2 is a 3-dimensional calibration curve for an inhibition immunoassay plotting optical absorbance of the assay solution versus toluene (antigen) concentration versus n-hexane (interferant) concentration.

The multiassay protocol of this invention begins with the preparation of calibrated solutions of antigen and interferant in water. These solutions are chosen to cover the range (area) of the antigen concentration versus interferant concentration matrix that the unknown samples are likely to fall into. A competition immunoassay and also a non-competition (either inhibition or sandwich) immunoassay is run on each of the calibrated antigen-interferant solutions. The readouts of the competition immunoassays on the calibrated solutions are entered into a computer program which interpolates between the calibrated points to produce interpolated points with estimated readout values. The calibrated points with actual measured competition immunoassay readouts and the interpolated points with estimated readouts define a 3-dimensional competition immunoassay calibration curve of readout versus antigen concentration versus interferant concentration (see example 1 and FIG. 1). Similarly the readouts of the non-competition (inhibition or sandwich) immunoassays on the calibrated solutions are entered into a computer program which interpolates between the calibrated points to produce interpolated points with estimated readout values. The calibrated points with actual measured non-competition immunoassay readouts and the interpolated points with estimated readouts define a 3-dimensional non-competition immunoassay calibration curve of readout versus antigen concentration versus interferant concentration (see example 2 and FIG. 2). In examples 1 (competition immunoassay) and 2 (inhibition immunoassay), the interpolation was performed using the cubic spline routine that came with MATLAB software.

An unknown sample is analyzed using the competition immunoassay and the non-competition immunoassay under the same conditions that were used to generate their respective 3-dimensional calibration curves. Points on the antigen concentration-interferant concentration matrix which have a readout on the 3-dimensional competition immunoassay calibration curve which is the same as the competition immunoassay readout for the sample are recorded and then plotted as a 2-dimensional curve of antigen concentration versus interferant concentration. Points on the antigen concentration-interferant concentration matrix which have a readout on the 3-dimensional non-competition immunoassay calibration curve which is the same as the non-competition immunoassay readout for the sample are recorded and then plotted as a 2-dimensional curve of antigen concentration versus interferant concentration. When the 2-dimensional curves for the competition immunoassay and the non-competition immunoassay are plotted on the same grid, they intersect at a point which represents the antigen concentration and the interferant concentration of the unknown sample.

If the antigen is known but the interferant is unknown, a known interferant (e.g., hexane) can be substituted for the unknown interferant in the generation of the 3-dimensional immunoassay calibration curve. The analysis of the unknown sample is performed in same way as described above. The point at which the 2-dimensional curves intersect gives the antigen concentration and the concentration of the substitute known interferant that causes the same interference as the unknown concentration of the unknown interferant.

If the antigen is unknown and the interferant is known, a known antigen (e.g., toluene) car be substituted for the unknown antigen in the generation of the 3-dimensional immunoassay calibration curve. The analysis of the unknown sample is performed in same way as described above. The point at which the 2-dimensional curves intersect gives the interferant concentration and the concentration of the substitute known antigen that has the same immunoassay activity as the unknown concentration of the unknown antigen.

Finally, if both the antigen and the interferant are unknown but their characteristics are somewhat known, more information can be obtained by substituting a similar known antigen and a similar known interferant in the generation of the 3-dimensional calibration curves. For example if there is a petroleum spill containing aromatic compounds and alkanes, toluene (antigen) and hexane (interferant) might be used to generate the 3-dimensional immunoassay calibration curves. The point at which the 2-dimensional curves intersect will provide the toluene concentration and hexane concentration that is equivalent to antigen/interferant antibody binding activity of the unknown petroleum sample.

The general nature of the invention having been set forth, the following examples are presented as specific illustrations thereof. It will be understood that the invention is not limited to these specific examples but is susceptible to various modifications that will be recognized by one of ordinary skill in the art.

In this work, toluene (Sigman, #27,037-7, 99.8% HPLC) was used as the antigen and hexane (Sigman, 27,050-4, 95+%, HPLC) was used as the interferant. Toluene was chosen for the antigen because the polychlonal rabbit antibodies used in these assays are most sensitive to toluene. N-hexane was chosen because it produces a relatively large interference effect. Samples containing from 0–100 ppm toluene and 0–2000 ppm hexane in 100 ml deionized water were prepared by pipetting the appropriate amount of toluene/hexane into the water and shaking the mixture vigorously for at least 30 sec. The results of the assays were found to be sensitive to the degree of mixing of the samples. Samples mixed vigorously for at least 30 seconds gave the most consistent results. Jars were kept closed when not in use to prevent evaporative losses. All incubations were done at room temperature.

The tests in the following examples 1–3 were performed using commercially available ELISA Total Petroleum Hydrocarbons in Water test kit (Strategic Diagnostics Inc., Newark, Del.). This consists of rabbit polyclonal antibodies against BTEX (benzene, toluene, ethylbenzene, and xylene) immobilized on the interior surface of polystyrene test tubes. A chromogenic enzyme-antigen conjugate (labeled antigen) is also provided in the kit.

In the following examples the antigen is toluene and the interferant is n-hexane.

Both competition and inhibition ELISA assays were performed on known calibration samples of various concentrations of toluene and hexane in water. These measurements were used as input data into a computer program which generated a 3-dimensional calibration curve of solution absorbance, measured by a spectrophotometer, versus toluene concentration and versus hexane concentration for the competition immunoassay and for the inhibition immunoassay.

EXAMPLE 1

Competition Immunoassay Calibration

Competition immunoassays were run on calibrated toluene-hexane water solutions using the following procedure. 500 µL of sample (containing toluene and hexane) and 100 µL of the chromogenic enzyme-antigen conjugate are added to the test tubes and incubated for 10 minutes. The sample-conjugate solution is then decanted and the test tube rinsed three times with deionized water. 500 µL of substrate is added to the test tube and incubated for 5 minutes. It reacts with any conjugate bound to antibody on the test tube wall, causing the color of the solution to change. The reaction is stopped using 500 µL of 1.0 N HCl. Absorbances were read at 450 nm using a differential spectrophotometer (Strategic Diagnostics Inc., Newark, Del.). The results of the competition immunoassay tests are summarized in Table 1, where the values given are the optical absorbances for the toluene-hexane pairs.

TABLE 1

Competition Immunoassay Calibration Results
(Optical Absorbency)

| Hexane Concentration⇒<br>⇓ Toluene Concentration | 0 ppm | 1000 ppm | 2000 ppm |
|---|---|---|---|
| 0 ppm | 0.72 | 0.36 | 0.24 |
| 25 ppm | 0.34 | 0.24 | 0.16 |
| 50 ppm | 0.18 | 0.10 | 0.08 |
| 75 ppm | — | — | — |
| 100 ppm | 0.12 | 0.07 | 0.06 |

The data in table 1 were interpolated to a matrix of 2 ppm in toluene concentration and 20 ppm in n-hexane concentration using the computer program listed below. The interpolation results are presented in FIG. 1 as a 3-dimensional calibration curve for the competition immunoassay showing optical absorbancy versus toluene concentration versus n-hexane concentration.

EXAMPLE 2

Inhibition Immunoassay Calibration

Inhibition immunoassays were run on calibrated toluene-hexane water solutions using the following procedure. The inhibition assay was performed by incubating 600 $\mu$L of sample (containing toluene and n-hexane) in the antibody coated test tube for 6 min. Then, the sample was decanted and the test tube rinsed three times to remove unreacted antigen. Following this, 500 $\mu$L of water and 100 $\mu$L of the chromogenic enzyme—antigen conjugate were incubated in the test tube for 6 min. Then, the conjugate/water solution was poured out and the test tube rinsed three times to remove unreacted conjugate. 500 $\mu$L of substrate is added to the test tube and incubated for 5 minutes. It reacts with any conjugate bound to antibody on the test tube wall, causing the color of the solution to change. The reaction is stopped using 500 $\mu$L of 1.0 N HCl. Absorbances were read at 450 nm using a differential spectrophotometer (Strategic Diagnostics Inc., Newark, Del.).

The results of the competition immunoassay calibration tests are summarized in table 2, where the values given are the optical absorbances for the toluene-hexane pairs.

TABLE 2

Inhibition Immunoassay Test Results
(Optical Absorbency)

| Hexane Concentration⇒<br>⇓ Toluene Concentration | 0 ppm | 1000 ppm | 2000 ppm |
|---|---|---|---|
| 0 ppm | 0.68 | 0.62 | 0.61 |
| 25 ppm | 0.52 | 0.56 | 0.55 |
| 50 ppm | — | — | — |
| 75 ppm | 0.46 | 0.51 | 0.50 |
| 100 ppm | 0.45 | 0.48 | 0.49 |

The data in table 2 were interpolated to a grid matrix of 2 ppm in toluene concentration and 20 ppm in n-hexane concentration using the computer program listed below. The interpolation results are presented in FIG. 2 as a 3-dimensional calibration curve for the inhibition immunoassay showing optical absorbancy versus toluene concentration versus n-hexane concentration.

Computer Programs

The data from the competition (Table 1) and inhibition (Table 2) assays was analyzed using the following programs which are written in MATLAB:

A. Analysis of Competition Assay:

```
load x
load y1
load xi2
load yi2
a1 = input('Absorbance in competitive assay')
load onepart.asc
onepart = interp1(y1, onepart, yi2, 'spline')
onepart = rot90(onepart, 3)
onepart = interp1(x, onepart, xi2, 'spline')
onepart = rot90(onepart, 1)
onepart = onepart − a1
onepart = abs(onepart)
[Y,I1] = min(onepart)
I1 = rot90(I1, 3)
I1 = I1*2
I1 = I1 − 2
plot(xi2, I1)
axis([0 2000 0 100])
title('Competitive Assay')
xlabel('Hexane Concentration (ppm)')
ylabel('Toluene Concentration (ppm)')
yy = [xi2, I1]
save test1.asc yy −ascii
``` b. Analysis of Inhibition Assay:

```
load x
load y1
load xi2
load yi2
a2 = input('Absorbance in blocking assay')
load twopart.asc
twopart = interp1(y1, twopart, yi2, 'spline')
twopart = rot90(twopart, 3)
twopart = interp1(x, twopart, xi2, 'spline')
twopart = rot90(twopart, 1)
twopart = twopart − a2
twopart = abs(twopart)
[Y,I2] = min(twopart)
I2 = rot90(I2, 3)
I2 = I2*2
I2 = I2−2
plot(xi2, I2)
axis([0 2000 0 100])
title('Blocking Assay')
xlabel('Hexane Concentration (ppm)')
ylabel('Toluene Concentration (ppm)')
yy = [xi2, I2]
save test2.asc yy −ascii
```

The programs require the following inputs:
i. A file in ASCII format which contains the antigen/interferant calibration matrix (absorbances), with the changing antigen concentration being the columns and the changing interferant concentration being the rows. The following is an example of an input file:
.72, .36, .24
.34, .24, .16
.18, .10, .08
.12, .07, .06
ii. The program requires the following input files be present in the home directory:
Filename: x (ASCII file containing uninterpolated interferant concentrations). For example:
0
1000
2000
10000
Filename: y1 (ASCII file containing uninterpolated antigen concentrations). For example:

0
25
50
100

Filename: xi2 (ASCII file containing interpolated interferant concentrations).

Filename: yi2 (ASCII file containing interpolated antigen concentrations).

iii. The program requests the user to enter the absorbance measured for the unknown sample.

The program outputs a file called test1.asc for the competition assay and test2.asc for the inhibition assay that contain the (interferant, antigen) concentration datapairs that result in the absorbance that was inputted into the program.

c. The interpolation was performed using the cubic spline routine that came with the MATLAB software.

EXAMPLE 3

Determining the Toluene Concentration and the n-hexane Concentration by Using the Competition and Inhibition Tests in Combination Three samples were made which contained arbitrary concentrations of toluene and n-hexane in water. These samples were analyzed using the competition test of example 1 and the inhibition test of example 2. The results are given in table 3.

TABLE 3

| | | Test samples | | |
|---|---|---|---|---|
| Sample # ⇓ | Actual Toluene Concentration | Actual Hexane Concentration | Absorbance Measured- Competitive Assay | Absorbance Measured- Inhibition Assay |
| 1 | 45 | 1600 | 0.12 | 0.52 |
| 2 | 25 | 0 | 0.34 | 0.52 |
| 3 | 25 | 1000 | 0.24 | 0.56 |

Figure 3:
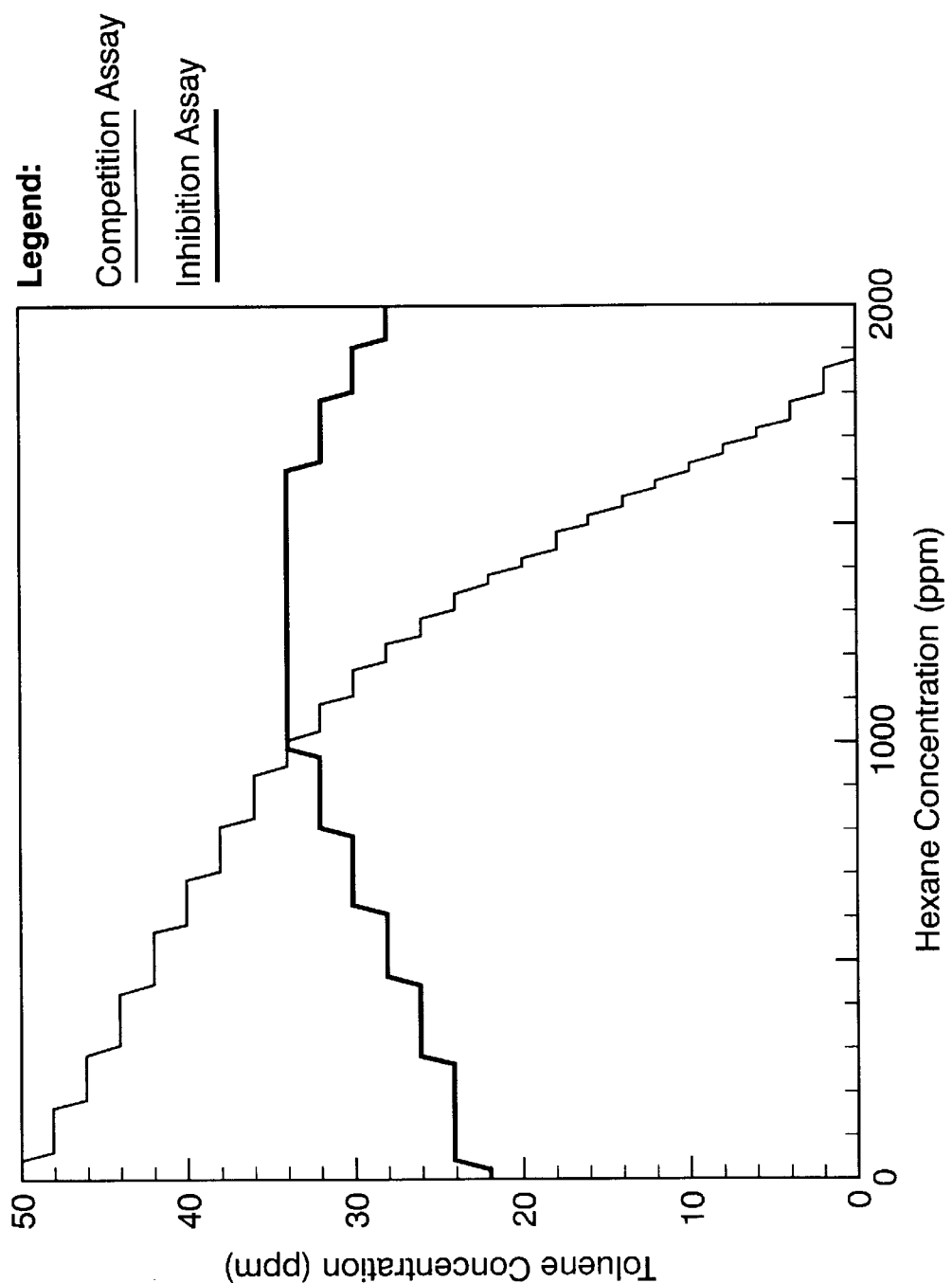
FIG. 3 shows two 2-dimensional plots of toluene (antigen) concentration versus hexane (interferant) concentration: one corresponding to the readout obtained for the sample in the competition immunoassay and the other corresponding to the readout obtained for the sample in the inhibition immunoassay.

For each of the 3 samples, the above computer program was used to do the following:

(1) From the 3-dimensional calibration curve for the competitive immunoassay (example 1), points on the toluene versus n-hexane concentration matrix which had the same absorbance as the competition immunoassay absorbance of the sample were recorded and then replotted as a 2-dimensional curve of toluene concentration versus n-hexane concentration. For example, FIG. 3 shows the 2-dimensional toluene versus hexane curve obtained from the competition immunoassay of sample #3.

(2) Similarly, from the 3-dimensional calibration curve for the inhibition immunoassay (see FIG. 2) points on the toluene versus n-hexane concentration matrix which had the same absorbance as the inhibition immunoassay absorbance for the sample were recorded and then replotted as a 2-dimensional curve of toluene concentration versus n-hexane concentration. For example, FIG. 3 shows the 2-dimensional toluene versus hexane curve obtained from the inhibition immunoassay of sample #3.

(3) the point of intersection of the two 2-dimensional curves (see FIG. 3) gave the toluene concentration and the n-hexane concentration. Results for the 3 samples are given in table 4.

TABLE 4

| Sample # | Actual Toluene Concentration | Actual Hexane Concentration | Measured Toluene Concentration | Measured Hexane Concentration |
|---|---|---|---|---|
| 1 | 45 | 1600 | 58 | 1050 |
| 2 | 25 | 0 | 34 | 0 |
| 3 | 25 | 1000 | 34 | 950 |

It can be seen from Table 4 that in fact the Multiassay Protocol works. Deviations of the measured value from the actual values result from measurement uncertainties in the calibration data and also the assays on the real samples. These uncertainties can be reduced by using a finer grid of toluene and hexane concentrations in the calibration data, and by taking multiple measurements at each concentration to reduce experimental error. Of course this new protocol assumes the sample only contains two constituents. For more complex samples, the new protocol can be used to obtain two pieces of information: the antigen concentration, and interferant concentration.

The present state of the art is to use either the competition or the inhibition assay to determine the antigen concentration. If an interferant is present it is not accounted for. This can lead to serious inaccuracies in the results of the assay. For example, the toluene concentration of the three samples described in the previous section could be determined using existing methods, i.e., the competition protocol recommended by the manufacturer. In this case, one would obtain the calibration curve in FIG. 1 for 0 ppm hexane. Using this curve and the measured absorbances, the toluene concentrations are determined for each sample, as given in Table 5. It can be seen that the toluene concentrations obtained by the old method are all too high: 122% high for sample 1, 36% high for sample 2, and 88% high for sample 3. The inaccuracy in sample 2 (the only one of the three samples with no hexane) results from inaccuracies in preparing the toluene in water suspension, and inaccuracy in the assay. This error is typical for an immunoassay. The inaccuracies in samples 1 and 3 are much higher than that for sample 2. The additional error is due to the presence of hexane: hexane causes an artificially high reading for the toluene concentration in the competition protocol. Using the new method, the accuracy of the measured toluene concentration is improved significantly: 29% high for sample 1, 36% high for sample 2 (there is no change in the accuracy for sample 2 because there was no hexane in this sample), and 36% high for sample 3. Furthermore, the new method provides information about the sample (the interferant concentration) previously unavailable. It should be emphasized that by using the Multiassay Protocol described in this Disclosure, it is possible to determine the concentration of a chemical species (hexane) in the sample that is not being bound by the antibody.

TABLE 5

| Sample # | Actual Toluene Concentration | Measured Toluene Concentration - Old Method | Measured Toluene Concentration - New Method |
|---|---|---|---|
| 1 | 45 | 100 | 58 |
| 2 | 25 | 34 | 34 |
| 3 | 25 | 47 | 34 |

By using the Multiassay Protocol, information about both the antigen and interferant concentration can be obtained, thus the assay yields more accurate results. This new method consists of using a combination of existing assay protocols (in the example described herein, the competition and inhibition), and the subsequent data analysis steps.

Numerous other modifications and variations of the present invention are possible in light of the foregoing teachings. It is therefore to be understood that within the scope of the appended claims the invention may be practiced otherwise than as specifically described.

What is claimed is:

1. A method for determining the concentration of a known target antigen and a known interferant in an unknown sample by using an antibody which reacts specifically with the target antigen and which does not react specifically with the interferant but wherein the interferant interferes with the reaction between the antibody and the target antigen, comprising:

A. preparing calibrated solutions of the target antigen and the interferant which cover a matrix of the concentration of the target antigen versus the concentration of the interferant, wherein the matrix covers the ranges of concentrations that the unknown sample is likely to fall into;

B. generating a 3-dimensional calibration curve for a competition immunoassay which shows the immunoassay readout for points on the matrix of the target antigen concentration versus the interferant concentration by
      a. using the antibody in a competition immunoassay on each of the calibrated solutions to obtain measured readouts for those solutions, wherein the competition immunoassay involves a reaction between the antibody and a labeled antigen competing with the reaction between the antibody and the target antigen, and wherein the interferant interferes with both reactions,
      b. using a computer program operating on the competition immunoassay readout values for the calibrated solutions to interpolate between the calibration points to produce interpolated points with estimated readout values, wherein the 3-dimensional calibration curve of the readout versus the target antigen concentration versus the interferant concentration is defined by the calibration points and the interpolated points;

C. generating a 3-dimensional calibration curve for a non-competition immunoassay selected from the group consisting of inhibition immunoassays and sandwich immunoassays which shows the non-competition immunoassay readouts for points on the matrix of the target antigen concentration versus the interferant concentration by
      a. using the antibody in a non-competition immunoassay on each of the calibrate solutions to obtain measured readouts for those solutions,
      b. using a computer program operating on the non-competition immunoassay readout values for the calibrated solutions to interpolate between the calibrated points to produce interpolated points with estimated readout values, wherein the 3-dimensional calibration curve of the readout versus the target antigen concentration versus the interferant concentration for the non-competition immunoassay is defined by the calibration points and the interpolated points;

D. performing the competition immunoassay on the unknown sample to obtain a competition immunoassay readout for the sample;

E. finding the matrix points (target antigen concentration versus interferant concentration) on the 3-dimensional calibration curve for the competition immunoassay which have the same readout as the unknown sample and using the points to form a 2-dimensional curve of the target antigen concentration versus the interferant concentration for the competition readout value for the unknown sample;

F. performing the non-competition immunoassay on the unknown sample to obtain a non-competition immunoassay readout for the sample;

G. finding the matrix points (target antigen concentration versus interferant concentration) on the 3-dimensional calibration curve for the non-competition immunoassay which have the same read out as the unknown sample and using the points to form a 2-dimensional curve of the target antigen concentration versus the interferant concentration for the non-competition readout value for the unknown sample; and H. plotting the 2-dimensional competition immunoassay curve and the 2-dimensional non-competition curve on the same 2-dimensional grid of the target antigen concentration versus the interferant concentration and determining the target antigen concentration and the interferant concentration corresponding to the point at which the two curves intersect which are the target antigen concentration and the interferant concentration of the unknown sample.

2. The method of claim 1 wherein the non-competition immunoassay is an inhibition immunoassay.

3. The method of claim 1 wherein the non-competition immunoassay is a sandwich immunoassay.

4. The method of claim 1 wherein a radioisotope label is used and the readouts are obtained with a scintillation counter.

5. The method of claim 1 wherein a fluorescent label is used and the readouts are obtained by fluorometry.

6. The method of claim 1 wherein an enzyme label is used and the readouts are obtained by spectrophotometry.

7. The method of claim 1 wherein a colloidal gold label is used and the readouts are obtained by a spectrophotometer or an electron microscope.

* * * * *